United States Patent [19]

Lindqvist et al.

[11] Patent Number: 5,681,825
[45] Date of Patent: Oct. 28, 1997

[54] SURGICAL METHOD

[76] Inventors: Bengt Lindqvist, Myskdalen, Funbo 755 97, Uppsala; Daniel Ogbonnaya, Daftövägen, PL 2514 452 96, Strömstad; Gillis Ponterius, Stenhagsvagen 86 752 60, Uppsala; Ove Wik, Handarbetsvägen 64 757 57, Uppsala, all of Sweden

[21] Appl. No.: 410,604

[22] Filed: Mar. 21, 1995

Related U.S. Application Data

[63] Continuation of Ser. No. 31,351, Mar. 15, 1993, abandoned, which is a continuation-in-part of Ser. No. 713,379, Jun. 13, 1991, abandoned.

[51] Int. Cl.$^6$ .................... A01N 43/04; A61K 31/715; A61F 13/00; A61F 2/00
[52] U.S. Cl. .................... 514/54; 514/912; 514/913; 514/954; 435/101; 424/422; 424/423; 424/427; 536/124; 536/123.1
[58] Field of Search .................... 514/54, 912, 913, 514/954; 424/422, 423, 427; 435/101; 128/899; 536/124, 123.1

[56] References Cited

U.S. PATENT DOCUMENTS

| | | | |
|---|---|---|---|
| 4,141,973 | 2/1979 | Balazs | 514/24 |
| 4,328,803 | 5/1982 | Pape | 514/54 |
| 4,486,416 | 12/1984 | Soll et al. | 424/180 |
| 4,517,295 | 5/1985 | Bracke et al. | 435/101 |
| 4,713,446 | 12/1987 | Devore et al. | 514/912 |
| 4,716,224 | 12/1987 | Sakurai et al. | 514/54 |
| 4,784,990 | 11/1988 | Nimrod et al. | 514/54 |
| 4,819,617 | 4/1989 | Goldberg et al. | 514/54 |
| 4,851,513 | 7/1989 | Devore et al. | 514/912 |
| 4,965,253 | 10/1990 | Goldberg et al. | 514/912 |
| 5,103,840 | 4/1992 | Kavoussi | 514/54 |
| 5,143,724 | 9/1992 | Leschiner et al. | 424/78.08 |

OTHER PUBLICATIONS

Obstbaum; "Ocular Surgery News"; vol. 8(12), p. 706–712, Jun. 15, 1990.

"The Scope of Hyaluronic Acid as an Experimental Intraocular Implant", Erwin Hultsch, *Ophthalmology*, vol. 87, No. 7, Jul. 1990, pp. 706–712.

*Primary Examiner*—Louise Leary
*Attorney, Agent, or Firm*—Dinsmore & Shohl LLP

[57] ABSTRACT

Methods of facilitating surgical operations that involve the eye or eye area comprise introducing an opthalmologically acceptable composition containing hyaluronic acid into the site of the surgical operation. The hyaluronic acid comprises a chemically unmodified sterilized hyaluronic acid substance having a weight average molecular weight of from 4,500,000 to 12,000,000 daltons, a zero shear viscosity of from 1,000 to 80,000 Pas as measured on a 1.3–1.6% (wv) solution of hyaluronic acid substance in physiological phosphate buffer, and an absorbance at 257 nm of less than 3.5 when measured on a 1% solution of hyaluronic acid substance in sodium chloride buffer in a 10 mm cuvette. Preferred sterilized solutions of hyaluronic acid comprise hyaluronic acid which is chemically unmodified from the naturally occurring hyaluronic acid and has a weight average molecular weight of from 4,500,000 to 8,000,000 daltons, a zero shear viscosity of from 1,000 to 20,000 Pas and an absorbance at 257 nm of less than 3.5.

12 Claims, No Drawings

SURGICAL METHOD

RELATED APPLICATION

This application is a continuation of application Ser. No. 08/031,351 filed Mar. 15, 1993 now abandoned, which is a continuation-in-part application of application Ser. No. 07/713,379 filed Jun. 13, 1991 now abandoned.

BACKGROUND

Hyaluronic acid (HA) is a naturally occurring glycosamino-glycan consisting of a linear polymer of repeating units of glucuronic acid and N-acetyl-glucosamine. The molecular weight can vary over a wide range depending on the source. Hyaluronic acid is present in several tissues of animals, and in some organs, such as rooster combs, in concentrations high enough for commercial scale extraction. Such tissue contains HA of a wide range of molecular weights and during a complex series of extraction, purification and sterilization steps, high molecular weight chains are more or less degraded resulting in a final product having a considerably narrower molecular weight range.

The critical parameters determining the characteristics of the final product in this respect are the molecular weight distribution of HA in the raw material, the degree of degradation of HA chains during the purification and sterilization process and the effectiveness of removing low molecular weight HA.

In the present specification the most commonly adopted name hyaluronic acid will be used. At neutral pH it exists as the salt hyaluronate. The name hyaluronan in accordance with modern nomenclature of polysaccharides has been suggested by Balazs et al (Biochem J. Vol. 235 (1986) p. 903).

The most appropriate way of expressing the molecular weight of a product of this type would be to present the complete molecular weight distribution curve. However, the parameter usually used is the weight average molecular weight value.

Due to the complex purification scheme required for obtaining an acceptable product from animal tissue, considerable efforts have been devoted to methods for producing HA from microorganisms, especially various Streptococcus strains (see for instance U.S. Pat. No. 4,897,349 and U.S. Pat. No. 4,784,990). The high molecular weight HA produced according to U.S. Pat. No. 4,784,990 has a molecular weight of about 3,500,000 to 4,000,000.

A commercially available hyaluronic acid product is HEALON® (Kabi Pharmacia AB, Uppsala Sweden) which has a weight average molecular weight of about 4,000,000 daltons. This product is produced as outlined in U.S. Pat. No. 4,141,973 and is an ultrapure product, characterized by infiltration by no more than about 200 white blood cells per $mm^3$ of aqueous humor of a monkey eye when one millilitre of a 1% solution of the sodium salt of the acid in physiological buffer is implanted in the vitreous replacing about one-half the existing liquid vitreous. This procedure is usually referred to as the "monkey eye test" and has become a standard test for viscoelastic products to be used in eye surgery.

HEALON® has been widely used for about ten years in cataract surgery procedures where it protects tissues against mechanical damage, provides space and permits manipulation of tissues during surgery.

There are many literature references relating to the use of viscoelastic products in ophthalmological applications and the preparation of such products, including the preparation of chemically modified HA. Chemical modification by treatment of the animal tissue containing HA with an aldehyde is described in U.S. Pat. No. 4,713,448. The present inventors prefer to not chemically modify animal tissue containing HA so as to avoid the risk that the resulting product could become immunogenic. One great advantage of using chemically unmodified HA in ophthalmological applications (in which there is a very high requirement for absence of side effects which could easily be fatal to the very sensitive tissues inside the eye) is that unmodified HA is a natural substance normally found in the eye. An unmodified HA is accordingly of special interest.

A concern in surgical operations on the eye which involve the injection of a viscous material (such as HA) into the eye area is the intraocular pressure (IOP) which occurs. (See Luther, Journ. Cataract Refract. Surg. Vol. 15, 1989, p. 415–420 and Alpar, Ophthalmic Surgery, 19-9, Vol. 1988, p. 636–642). It would be expected that the higher the viscosity of the material injected into the eye area the greater would be the increase in intraocular pressure—and that it would therefore not be desirable to increase the viscosity (i.e. the molecular weight) of the commercially available products such as HEALON® (which as indicated previously has a weight average molecular weight of about 4,000,000).

THE PRESENT INVENTION

We have unexpectedly found that an HA having a high viscosity and a high weight average (4,000,000 to 12,000,000) can be quite satisfactorily used for injection into the eye area during operations on the eye provided that the zero shear viscosity of the HA injected into the eye area is in the range of about 700 to about 20,000 Pas. (Zero shear rate is the viscosity at minimal shear rate, i.e. the resistance that is offered from immobility to starting flow.)

The zero shear viscosity of the HA which we use in our method is about 10 times that of HEALON®, resulting in a considerably higher ability to maintain the chamber space and to remain in the injection area even in cases of fairly broad incisions. Our preparation is, in spite of that, nearly as easy as HEALON® for the surgeon to inject into the appropriate part of the eye, to manipulate and to aspirate. A problem with increased intraocular pressure was feared, but surprisingly it did not occur. Comparative clinical studies with our composition and HEALON® in 200 patients undergoing cataract surgery with lens implantation showed no increase in intraocular pressure with our composition. We found it very easy to aspirate/irrigate out the eye.

New high viscosity hyaluronic acid has been found to be more beneficial in connection with phacoemulsification surgery than the prior art products since it seems to protect the cornea much better. The probable reason for this is that it is more efficiently bound to the endothelium layer. Binding of hyaluronate to corneas and endothelial cells is reported by Madsen et al in Invest. Ophthalmol & Visual Sci. Vol. 30 (10) 2122-7.

In several clinical studies our composition has been found to be more effective than commercial HEALON® in that better anterior chamber depth can be obtained and maintained during surgery and in that eyes with small pupils are easier to operate on. The high force that can be applied on tissue surfaces is also of advantage in what is sometimes called "viscoexpression", when the lens is released from the bag surface. This technique is described by Corydon and Thim in J Cataract Refract Surg. Vol. 17 (1991) p. 628–632.

The HA substance of the present invention has the following specifications:

weight average molecular weight $\geq 6,200,000$ daltons, especially 6,200,000 to 12,000,000 daltons
hyaluronate $\geq 80\%$
loss on drying $\leq 20\%$
limiting viscosity number: $\geq 4.7$ m3 kg$^{-1}$
protein $\leq 3.6$ mg/g
iron $\leq 0.2$ mg/g
copper $\leq 0.2$ mg/g
acetone $\leq 5$ mg/g
chloroform $\leq 2$ mg/g
ethanol $\leq 10$ mg/g
bacterial endotoxins $\leq 0.5$ EU/14 mg
microbial total count $\leq 10$ microorganisms/20 mg The HA preparation of the present invention is prepared, optionally under aseptic conditions, by dissolving an amount of the HA substance in an aqueous solution, such as a physiological phosphate buffer to a HA concentration of 1.3–1.6% (w/v) and is characterized by having a zero shear viscosity $\geq 3,000$ Pas (Pascal seconds), especially in the range of from 3,000–80,000 Pas.

The absorbance at 257 nm is less than 3.5 when measured on a 1% solution in a 10 mm cuvette. The preparation further passes the monkey eye test as defined in U.S. 4,141,973, and which is also summarized in the prior art description above. The preparation is pyrogen free and the amount of bacterial endotoxins is less than 0.5 EU/ml. For other characterizing parameters see the values given above in connection with the definition of the solid substance.

The buffer (about pH 7.3) may preferably be a physiological phosphate solution containing 0.276 g $Na_2HPO_4 \cdot 2H_2O$, 0.0395 g $NaH_2PO_4 \cdot H_2O$, and 8.476 g NaCl1 per 1,000 ml.

In a further aspect of the invention said HA preparation is sterilized, for instance by treatment in an autoclave. The molecular weight of HA in a sterilized product is, as mentioned above, lowered due to degradation during the sterilization step. The weight average molecular weight in the present case is in the range of from about 4,000,000 to 8,000,000 daltons, in particular from 4,500,000 to 6,500,000 daltons. The zero shear viscosity is $\geq 700$ Pas, especially in the range of from about 700 to about 20,000 Pas, and preferably from 1,000 to 9,000 Pas.

HA products or preparations according to the invention, aseptically produced as well as sterilized, have a broad range of applications in various types of surgery. The sterilized preparation is, however, at present mainly intended for use in demanding surgical procedures in the anterior segment of the eye. When it is injected into this segment a deep anterior chamber is created which is further maintained throughout surgery so as to allow safe manipulation with minimized trauma to the corneal endothelium and other tissues. Due to its viscosity and elasticity it can be used to maneuver, separate and control tissues, thus allowing specific and atraumatic manipulation of the ocular tissues. The high viscosity is also particularly important for providing an appropriate counter pressure in cases where there is high pressure on the globe. The product can in these cases be used to push back an iris prolapse or a bulging vitreous.

One area of special interest is related to the use of soft intraocular lenses which are implanted through a very small incision, a technique of increasing importance. The lenses are kept folded during implantation and in the eye they are allowed to unfold. During this step the need to protect the surrounding tissues is even more pronounced compared to traditional implantation of PMMA lenses. The high viscosity product of the present invention will make this procedure easier for the surgeon and accordingly safer for the patient.

Isolating on a commercial scale a very high molecular fraction fulfilling the requirements for an ophthalmologically acceptable product was a real challenge and no such product was available until we were able to produce our high viscosity HA preparation.

A procedure for preparing a product according to the present invention is a follows:

EXAMPLE 1 a) Pretreatment of Rooster combs

Rooster combs were extensively washed in 70% ethanol, thoroughly rinsed in pure water and after another washing in 70% ethanol they were finally frozen. The frozen combs were sliced in a slicing machine to slices with a thickness of about 1–2 mm, which were kept frozen until further use.

b) Extraction of HA from tissue and purification thereof

The sliced and frozen combs tissue were thawed and about 750 g were taken out for further processing. 5000 ml 99.5% ethanol and 18 g of cetylpyridium chloride were mixed and the tissue was added to the mixture which was slowly stirred for about 8 hours. This step was repeated once but without the addition of cetylpyridium chloride and for 16 hours.

The now well washed comb tissue was added to a mixture of 4500 ml distilled water, 500 ml 99.5% ethanol and 2 g sodium hydroxide. The mixture was stirred slowly for about 20 hours. 300 g sodium chloride was added to the collected water extract which was then filtered on a 70µ Pall patrone filter. The filtered solution was precipitated in 99.5% ethanol and the precipitate was thereafter dissolved in a mixture of 150 g sodium chloride in 3000 ml distilled water.

The aqueous solution was then subjected to chloroform extraction (1:1) which was repeated three times, whereupon the sodium hyaluronate was precipitated from the aqueous phase with 99.5% ethanol. The precipitate was dissolved in about 2500 ml 0.1M sodium chloride solution which was then filtered on a 0.6µ Pall patrone filter. The filtered sodium hyaluronate solution was finally precipitated from the aqueous phase with 99.5% ethanol and washed twice in both ethanol and acetone. The pure white thready fiber was dried in a room temperature vacuum drier.

The HA contents in the dry fiber was 86%, the protein contents 0.5 mg/g, the absorbance at 257 nm (1% solution) 0.4 and the limiting viscosity number 5.8 m$^3$/kg. The weight average molecular weight was 9,000,000 daltons, as determined by low angle laser light scattering.

This experiment was repeated five times with different rooster comb material. The process was also scaled up to 32 kg and 96 kg rooster comb material, respectively, with equally good results.

The analysis of fifteen batches gave the following mean values with the total range given within parenthesis:
HA content: 86% (range 80–90%)
Protein: 0.8 mg/g (range 0.5–1.1 mg/g)
Absorbance (257 nm, 1%): 0.9 (range 0.4–2.0)
Limiting viscosity number (determined in an Ubbelohde viscometer with a mean shear rate for solvent of 1200 1/s at 25° C. using 0.15M NaCl as diluent): 5.7 m$^3$/kg (range 5.1–6.7 m$^3$/kg) M$_w$ (unsterilized): 8.0×10$^6$ daltons (range 6.7–9.8×10$^6$ daltons).

A HA preparation that could be used for instance in eye surgery was obtained by dissolving 1.3 g of a dry HA product as prepared above in 100 ml of a pH 7.3 phosphate buffer (0.276 g $Na_2HPO_4 \cdot 2H_2O$, 0.0395 g $NaH_2PO_4 \cdot H_2O$, and 8.476 g NaCl per 1,000 ml), whereupon the product was sterilized in an autoclave.

The weight average molecular weight from 6 preparations, sterilized by treatment in an autoclave, was 5.0, 4.7, 5.5, 5.7, 5.0 and 5.4×10$^6$ daltons, respectively.

The clinical advantage of using our high viscosity HA in eye surgery have been reported in some detail by Stephen A. Obstbaum in Ocular Surgery News (Volume 8(12), Jun. 15, 1990). The product on which his article is based is a product according to the present invention but the product was not commercially available when his article was published. The need for high viscosity materials is also mentioned in articles by Miller D and Stegmann R (Ocular Surgery News Volume 8 (1990) March 1) and Eisner G (Eur J Implant Refract Surg. Vol. 1 (1989) p 221–114).

What we claim is:

1. In a method of facilitating surgical operations that involve the eye or eye area by introducing an ophthalmologically acceptable composition containing hyaluronic acid into the site of the surgical operation, the improvement comprising introducing into the site of the operation a chemically unmodified sterilized hyaluronic acid substance having the following properties:

(1) weight average molecular weight of from 4,500,000 to 12,000,000 daltons, (2) zero shear viscosity from 1,000 to 80,000 Pas as measured on a 1.3–1.6% (wv) solution of hyaluronic acid substance in physiological phosphate buffer, and (3) absorbance at 257 nm of less than 3.5 when measured on a 1% solution of hyaluronic acid substance in sodium chloride buffer in a 10 mm cuvette.

2. The method according to claim 1, wherein the weight average molecular weight of the hyaluronic acid is from 4,500,000 to 8,000,000 daltons and the zero shear viscosity is from 1,000 to 20,000 Pas.

3. The method according to claim 1, wherein the hyaluronic acid has a weight average molecular weight of from 4,500,000 to 6,500,000 daltons and the zero shear viscosity is from 1,000 to 9,000 Pas.

4. The method according to claim 1, wherein the hyaluronic acid has a weight average molecular weight of between 4,700,000 and 5,700,000 daltons.

5. A method of facilitating surgical operations that involve the eye or eye area, the method comprising obtaining a naturally occurring hyaluronic acid, dissolving the naturally occurring hyaluronic acid in solution, sterilizing the resulting solution of hyaluronic acid, and introducing an ophthalmologically acceptable composition containing the sterilized solution of hyaluronic acid into the site of a surgical operation in the eye or eye area, the hyaluronic acid in the sterilized solution being chemically unmodified from the naturally occurring hyaluronic acid and having the following properties:

(1) weight average molecular weight of from 4,500,000 to 8,000,000 daltons, (2) zero shear viscosity from 1,000 to 20,000 Pas as measured on a 1.3–1.6% (wv) solution of the hyaluronic acid in physiological phosphate buffer, and (3) absorbance at 257 nm of less than 3.5 when measured on a 1% solution of the hyaluronic acid in sodium chloride buffer in a 10 mm cuvette.

6. The method according to claim 5, wherein the naturally occurring hyaluronic acid is dissolved in an aqueous solution.

7. The method according to claim 6, wherein the naturally occurring hyaluronic acid is dissolved in an aqueous solution comprising a physiological phosphate buffer.

8. The method according to claim 6, wherein the aqueous solution contains 1.3–1.6% (w/v) of the hyaluronic acid.

9. The method according to claim 5, wherein the solution of hyaluronic acid is sterilized in an autoclave.

10. The method according to claim 5, wherein the naturally occurring hyaluronic acid is obtained as an extract from rooster comb.

11. A sterilized solution of hyaluronic acid, the hyaluronic acid in the sterilized solution being chemically unmodified from the naturally occurring hyaluronic acid and having the following properties:

(1) weight average molecular weight of from 4,500,000 to 8,000,000 daltons, (2) zero shear viscosity from 1,000 to 20,000 Pas as measured on a 1.3–1.6% (wv) solution of the hyaluronic acid in physiological phosphate buffer, and (3) absorbance at 257 nm of less than 3.5 when measured on a 1% solution of the hyaluronic acid in sodium chloride buffer in a 10 mm cuvette.

12. The sterilized solution of hyaluronic acid according to claim 11, prepared by the steps of obtaining a naturally occurring hyaluronic acid, dissolving the naturally occurring hyaluronic acid in solution, and sterilizing the resulting solution of hyaluronic acid.

* * * * *